United States Patent
Jamilian et al.

(10) Patent No.: US 8,414,291 B1
(45) Date of Patent: Apr. 9, 2013

(54) METHOD AND SYSTEM FOR TREATMENT OF MAXILLARY DEFICIENCY USING MINISCREWS

(75) Inventors: Abdolreza Jamilian, Tehran (IR); Abdulrahman Showkatbakhsh, Tehran (IR)

(73) Assignee: Abdolreza Jamilian, Tehran (IR)

( * ) Notice: Subject to any disclaimer, the term of this patent is extended or adjusted under 35 U.S.C. 154(b) by 0 days.

(21) Appl. No.: 13/314,183

(22) Filed: Dec. 8, 2011

(51) Int. Cl.
*A61C 7/10* (2006.01)

(52) U.S. Cl.
USPC .................................. 433/7; 433/19

(58) Field of Classification Search ............... 433/7, 18, 433/24, 173, 174
See application file for complete search history.

(56) References Cited

U.S. PATENT DOCUMENTS

| | | | | |
|---|---|---|---|---|
| 4,026,023 | A * | 5/1977 | Fisher | 433/7 |
| 5,002,485 | A * | 3/1991 | Aagesen | 433/7 |
| 5,885,290 | A * | 3/1999 | Guerrero et al. | 606/71 |
| 5,921,774 | A * | 7/1999 | Kanomi et al. | 433/18 |
| 6,193,509 | B1 * | 2/2001 | DeVincenzo | 433/18 |
| 6,334,771 | B1 * | 1/2002 | Liou | 433/7 |
| 6,354,834 | B2 * | 3/2002 | Kanomi et al. | 433/18 |
| 6,358,255 | B1 * | 3/2002 | Testa | 606/105 |
| 6,575,742 | B2 * | 6/2003 | Kyung et al. | 433/18 |
| 6,827,574 | B2 * | 12/2004 | Payton | 433/8 |
| 7,329,121 | B2 * | 2/2008 | De Clerck | 433/18 |
| 2002/0025502 | A1 * | 2/2002 | Williams | 433/19 |
| 2004/0081937 | A1 * | 4/2004 | Graham | 433/19 |
| 2005/0227197 | A1 * | 10/2005 | Lin | 433/18 |
| 2006/0172251 | A1 * | 8/2006 | Voudouris | 433/18 |

* cited by examiner

*Primary Examiner* — Ralph Lewis

(57) ABSTRACT

A method and system for treatment of maxillary deficiency using miniscrews including placement of self drilling Titanium alloy miniscrews in the lower jaw, and Class III elastic tractions connecting the miniscrews to a tightly fitting upper removable appliance. The method intensifies correction of maxillary deficiency and increases convenience of the device usage.

1 Claim, 2 Drawing Sheets

METHOD AND SYSTEM FOR TREATMENT OF MAXILLARY DEFICIENCY USING MINISCREWS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The invention relates to orthopedic correction of maxillary deficiency. Skeletal Class III malocclusion is one of the most difficult discrepancies to correct. It can be defined as skeletal facial deformities characterized by maxillary deficiency, mandibular protrusion, or a combination of both. In subjects with maxillary deficiency where the mandible is not markedly affected, treatment may involve stimulation and guidance of maxillary growth by orthopaedic forces. Various types of extraoral appliances such as facemasks (U.S. Pat. No. 4,988,291 and D308,096) and protraction headgears (U.S. Pat. No. 7,121,824) have been used to correct maxillary deficiency. Such extraoral appliances are particularly unpleasant to wear. In order to overcome this disadvantage De Clerck invented an orthodontic implant (U.S. Pat. No. 7,329,121) which makes it possible to gradually move a person's maxilla to forward position by exerting an almost continuous pressure force or tensile force on the teeth. According to that invention the use of extra oral appliances is no longer necessary. However, the placing of the implant according to the invention on the lower or upper jaw requires a small surgical incision.

BRIEF SUMMARY OF THE INVENTION

To eliminate the problems associated with previously used extraoral appliances and to avoid the small surgery needed for placement of miniplates, I have developed a new method. In this method I place miniscrews in the lower jaw and an upper removable appliance in the upper jaw. I used Class III elastics to connect miniscrews to the upper removable. With this method there would be no need for any surgery and the small size would be very favorable for the patients.

DETAILED DESCRIPTION OF THE INVENTION

Figure 1:
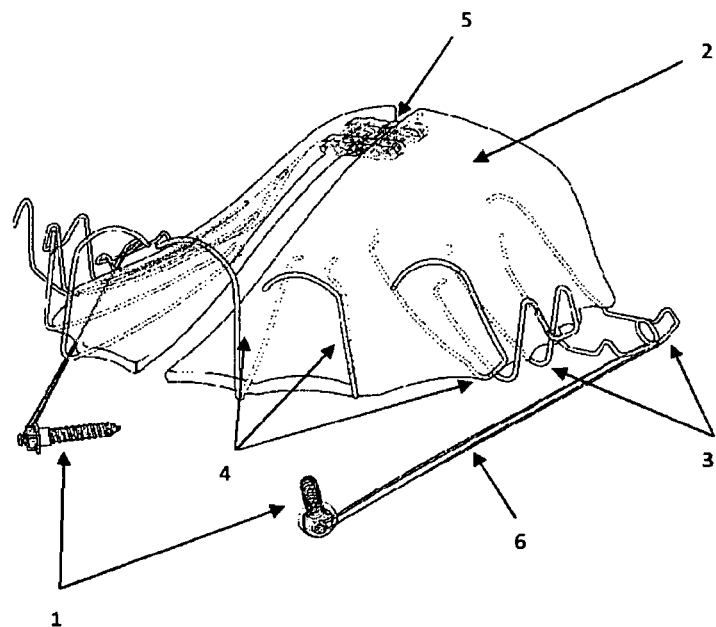
FIG. 1 is a schematic view in perspective of the upper removable appliance, miniscrews, and class III elastics according to the invention.
Figure 2:
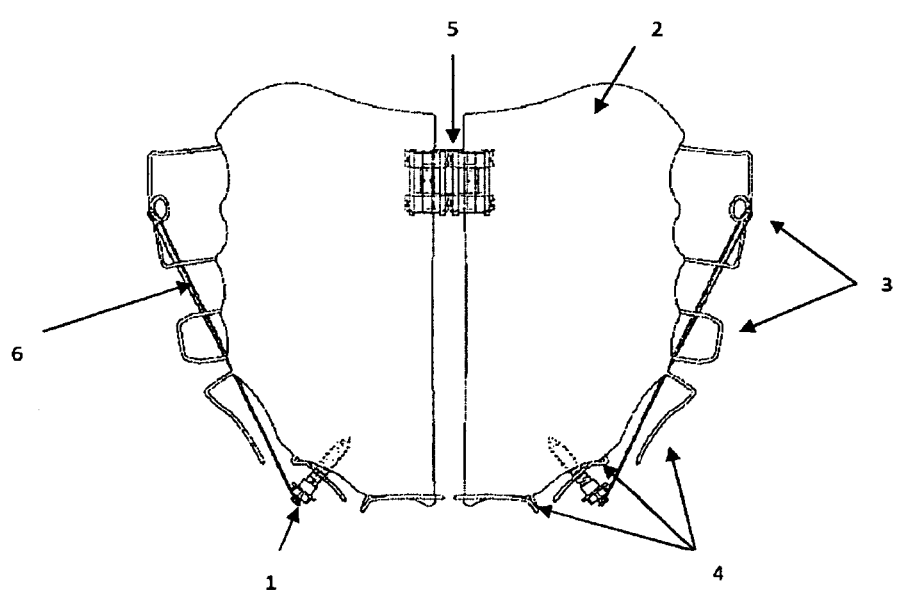
FIG. 2 is a schematic top view in perspective of the upper removable appliance, miniscrews, and class III elastics according to the invention.
Figure 3:
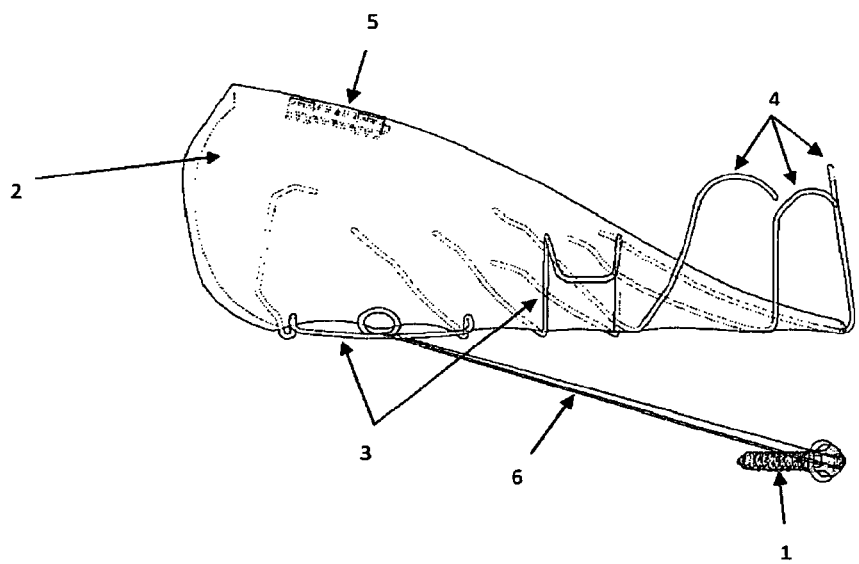
FIG. 3 is a schematic side view in perspective of the upper removable appliance, miniscrews, and class III elastics according to the invention.
Figure 4:
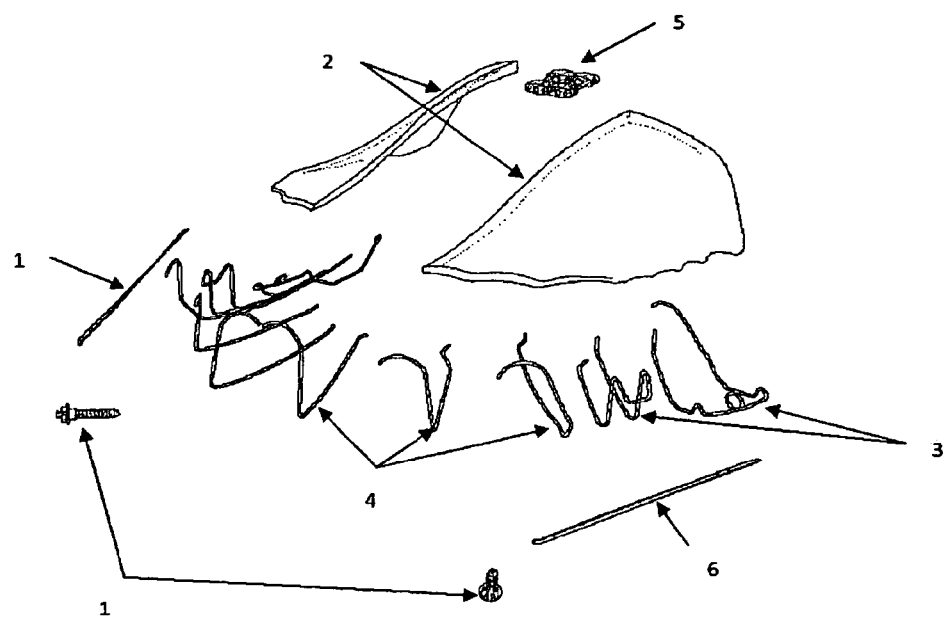
FIG. 4 is a schematic exploded view in perspective of the upper removable appliance, miniscrews, and class III elastics according to the invention.

Self-drilling Titanium Alloy Jeil™ miniscrews 1 (Jeil Medical Corp., Seoul, Korea) with 1.6 mm diameter and 8 mm length were placed under local anesthesia into the buccal alveolar bone between the mandibular canine and first premolar roots on both sides. The ideal position for screw insertion was evaluated by using a panoramic radiograph in order to avoid damage to the roots of the adjacent teeth and mental foramen. A tightly fitting upper removable appliance 2 was fabricated with hooked orthodontic clasps 3 on the upper first permanent molars and premolars and orthodontic clasps 4 on the upper permanent. An expansion screw 5 was placed in the midpalatal area of the upper removable appliance in order to loosen the nasomaxillary sutures for better movement of the maxilla. Miniscrews 1 were connected to the hooks of the clasps 3 of the removable appliance 2 by medium size orthodontic latex elastics 6 in order to generate ~350 g of anterior retraction.

In my method I place self drilling Titanium alloy miniscrews 1 with 50 to 70 degrees of angle in order to avoid loosening of the miniscrews. The angles chosen can achieve the best stability of miniscrews in the bone (Am. J. Orthod. Dentofac. Orthop. 139:628, 2011).

The invention claimed is:

1. A method for correction of a patient's maxillary deficiency, comprising:

inserting self-drilling titanium alloy miniscrews having a 1.6 mm diameter and an 8 mm length in a patient's buccal alveolar bone between the mandibular canine and first premolar roots on both sides of the lower jaw, wherein the miniscrews are angled 50 to 70 degrees in relation to buccal area surface, positioning a tightly fitting upper removable appliance in the patient's upper jaw wherein the removable appliance includes an expansion screw in the midpalatal area, hooked clasps on the upper first permanent molars, and clasps on the upper permanent canines and central incisors, and connecting orthodontic latex elastics between the miniscrews and the hooked clasps of the removable appliance.

* * * * *